(12) United States Patent
Bhandarkar et al.

(10) Patent No.: US 8,860,753 B2
(45) Date of Patent: Oct. 14, 2014

(54) VIRTUAL SURGICAL SYSTEM AND METHODS

(75) Inventors: Suchendra M. Bhandarkar, Athens, GA (US); Ernest William Tollner, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1589 days.

(21) Appl. No.: 11/578,258

(22) PCT Filed: Apr. 13, 2005

(86) PCT No.: PCT/US2005/012504
§ 371 (c)(1),
(2), (4) Date: Oct. 12, 2006

(87) PCT Pub. No.: WO2005/112563
PCT Pub. Date: Dec. 1, 2005

(65) Prior Publication Data
US 2007/0208234 A1    Sep. 6, 2007

Related U.S. Application Data

(60) Provisional application No. 60/561,584, filed on Apr. 13, 2004.

(51) Int. Cl.
| | |
|---|---|
| *G09G 5/30* | (2006.01) |
| *G06T 7/00* | (2006.01) |
| *G06F 19/00* | (2011.01) |
| *A61B 19/00* | (2006.01) |

(52) U.S. Cl.
CPC ............. *A61B 19/52* (2013.01); *G06F 19/3418* (2013.01); *A61B 19/50* (2013.01); *A61B 19/2203* (2013.01); *A61B 19/56* (2013.01); *A61B 2019/5238* (2013.01); *G06T 7/0012* (2013.01); *G06F 19/3437* (2013.01); *G06T 2207/30008* (2013.01); *A61B 2019/5236* (2013.01); *G06T 2207/10081* (2013.01)
USPC .......................................................... 345/619

(58) Field of Classification Search
CPC ...................................................... G06T 11/00
USPC ................................... 345/619; 382/378, 132
See application file for complete search history.

(56) References Cited

U.S. PATENT DOCUMENTS 5,951,475 A * 9/1999 Gueziec et al. ............... 600/425
6,701,174 B1 * 3/2004 Krause et al. ................. 600/407

(Continued)

OTHER PUBLICATIONS

Messmer et al. Interactive preoperative planning of internal fixation on a virtual 3D model, presented Fourth Annual North American Program on Computer Assisted Orthopaedic Surgery Jun. 15-17, 2002.*

(Continued)

*Primary Examiner* — Javid A Amini
(74) *Attorney, Agent, or Firm* — Thomas | Horstemeyer, LLP

(57) ABSTRACT

A virtual surgical system receives an image, such as a computer tomography (CT) scan, of an area of the patient in need of surgical reconstruction prior to an incision being made in a surgery. Bone fragments that are to be reduced are automatically selected using the virtual surgical system. The system performs surface matching techniques using surface data representing the contour of the end surfaces of the fragments to determine how the corresponding fragments should be oriented to perform the reduction. At least one of the fragments may then be transformed (e.g. via translation and/or rotation) to join the surfaces based on the matched surfaces. An image may be generated of the reconstructed area providing a virtual representation of a reconstructed object. Thus, before actual dissection of the area, and the subsequent physical surgical reduction of the bones, an image of the reconstructed object may be displayed such that a prosthesis may be determined and/or manufactured.

23 Claims, 8 Drawing Sheets

(56) References Cited

U.S. PATENT DOCUMENTS

| | | | | |
|---|---|---|---|---|
| 6,711,432 | B1* | 3/2004 | Krause et al. | 600/427 |
| 7,027,642 | B2* | 4/2006 | Rubbert et al. | 382/154 |
| 7,274,810 | B2* | 9/2007 | Reeves et al. | 382/128 |
| 7,427,200 | B2* | 9/2008 | Noble et al. | 434/274 |
| 7,837,621 | B2* | 11/2010 | Krause et al. | 600/300 |
| 2005/0004450 | A1* | 1/2005 | Ben-Haim et al. | 600/424 |
| 2007/0169782 | A1* | 7/2007 | Smothers et al. | 128/898 |

OTHER PUBLICATIONS

Determining Acetabular Cup Position Following Total Hip Replacement, B. Jaramaz1,2, L. J. Cassenti2, T. J. Levison, C. Nikou, and A. M. DiGioiaCenters for Medical Robotics and Computer Assisted Surgery, UPMC Shadyside Hospital, Pittsburgh, PA and Carnegie Mellon University, 3 pages, 2002.*

Long Bone Panoramas From Fluoroscopic X-Ray Images Ziv Yaniv, Student Member, IEEE and Leo Joskowicz, Senior Member, IEEE, 2004.*

Messmer, et al., Interactive Preoperative Planning of Internal Fixation on a Virtual 3D Model, presented Fourth Annual North American Program on Computer Assisted Orthopaedic Surgery, Jun. 15-17, 2002.*

Long, et al., 3D Model of Long Bone from Two X-Ray Images by Matching with 2D/3D Database, presented Fourth Annual North American Program on Computer Assisted Orthopaedic Surgery, Jun. 15-17, 2002.*

* cited by examiner

VIRTUAL SURGICAL SYSTEM AND METHODS

CROSS-REFERENCE TO RELATED APPLICATIONS

This application claims priority to, and the benefit of, U.S. Provisional Patent Application entitled "Virtual Surgical Systems and Methods," assigned Ser. No. 60/561,584, and filed on Apr. 13, 2004, which is incorporated by reference in its entirety.

TECHNICAL FIELD

The present disclosure is generally related to computer systems and, more particularly, is related to computer systems for virtual surgery implementations.

BACKGROUND

Traumatic impact of the skeleton may require extensive surgery to re-align fragmented skeletal features. Although any alignment of bone fragments requires a degree of precision, restoring the form and function of the bone fragments in the craniofacial skeleton is particularly challenging because of the strict tolerances required. During conventional craniofacial surgery, a plastic surgeon restores the form and function of the bone fragments in the craniofacial skeleton by first exposing all the fragments (e.g. by removing any fleshy tissue surrounding the fragments). This visualization is necessary to determine how the bone fragments should fit together for a reduction of the bone fragments. Next, the bone fragments are reduced by bringing the displaced or broken bones to a desired configuration position (e.g. returned back to their pre-fractured positions). The reduction is typically performed by manually manipulating the bone fragments to the desired configuration. Once the bone fragments are reduced, the reduced bone fragments are maintained in this configuration with a prosthesis.

The prosthesis, may be, for example, rigid screws and plates and/or bone grafts, which are used to maintain the reduced bone pieces together. The screws, plates, and/or grafts may be made of metals or synthetic materials, such as plastics. Typically, the decision as to the type and configuration (e.g. dimensions, form, rigidity, etc.) of the prosthesis is made during the surgical procedure such that the surgeon has a visual depiction of the contours of the fragments once reduced. The surgeon can then use this visual depiction to determine the type and configuration of the prosthesis. A machine room may be located in close proximity to the operating room to fabricate the necessary prosthesis during the operation.

There are several problems with this current, standard approach. To visualize the fragments (e.g. in order to reduce them and to determine the prosthesis to use) necessitates their exposure, which reduces the blood supply to the bodily area of the fracture. To improve the blood supply, the surgeon can decrease the extent of dissection. However, with decreased dissection, the surgeon not being able to visualize the entire fracture, which could lead to potential mal-alignments of the bone fragments. Further, because the surgeon does not determine the type and configuration of the prosthesis to use until the surgery is underway, the surgery is prolonged while the prostheses is configured or manufactured appropriately. This results in extended periods of time in which the patient remains dissected, increasing the chance of surgical complications and tying up valuable surgical resources such as surgical clean rooms, surgeons, nurses, and anesthesiologists, etc.

Accordingly, techniques for providing a pre-operative visualization of the movement needed to actually reduce the bone fragments to the desired position, and of the bone fragments once reduced, are needed.

BRIEF DESCRIPTION OF THE DRAWINGS

Many aspects of a computer-aided virtual (i.e., in silico) surgical system and the underlying methods can be better understood with reference to the following drawings. The components in the drawings are not necessarily to scale, emphasis instead being placed upon clearly illustrating the principles of a virtual surgical system and the underlying methods. Moreover, in the drawings, like reference numerals designate corresponding parts throughout the several views.

SUMMARY

Figure 1:
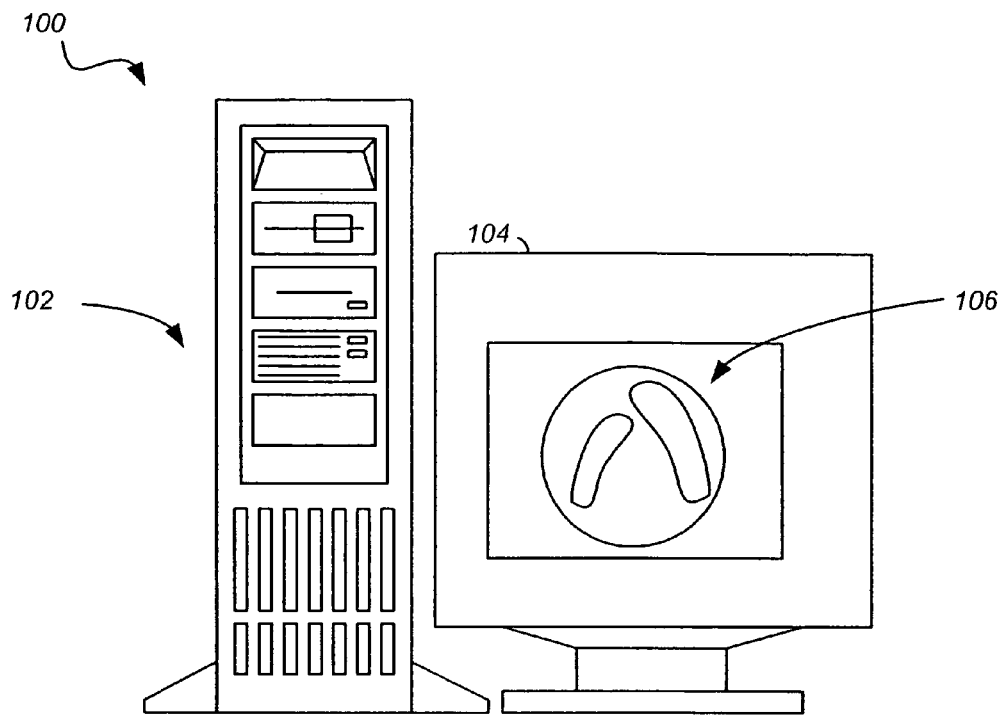
FIG. 1 is an embodiment of a computer system that may be used to implement an embodiment of a virtual surgical system.

Systems and methods for providing virtual alignment of fractured surfaces are provided.

One embodiment of a method for providing virtual alignment of fractured surfaces includes matching at least two fragment surfaces of a fractured object based on surface data of each of the fragment surfaces, the surface data representing the contour of each of the at least two fragment surfaces. The method further includes determining a transformation that places the at least two fragment surfaces in three-dimensional alignment to form a reconstructed object. The method further includes generating an image of the reconstructed object. The image of the reconstructed object includes the at least two fragments aligned by the transformation.

One embodiment of a virtual surgical system includes a memory and a processor. The memory including instructions for providing virtual alignment of fractured surfaces. The processor is configured to execute the instructions to match at least two fragment surfaces of a fractured object based on surface data of each of the fragment surfaces. The surface data represents the contour of each of the at least two fragment surfaces. The processor is further configured to determine a transformation that places the at least two fragment surfaces in three-dimensional alignment to form a reconstructed object, and to generate an image of the reconstructed object. The image of the reconstructed object includes the at least two fragments aligned by the transformation.

Yet another embodiment includes a computer-readable medium having a computer program for providing virtual alignment of fractured surfaces. The computer readable medium includes logic configured to match at least two fragment surfaces of a fractured object based on surface data of each of the fragment surfaces, the surface data representing the contour each of the at least two fragment surfaces. The computer-readable medium further includes logic configured to determine a transformation that places the at least two fragment surfaces in three-dimensional alignment to form a reconstructed object. The computer-readable medium further includes logic configured to generate an image of the reconstructed object. The image of the reconstructed object includes the at least two fragments aligned by the transformation.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

DETAILED DESCRIPTION

Embodiments of virtual surgical systems, and the underlying methods, are disclosed (herein referred to as a virtual surgical system for brevity). The virtual surgical systems may be used for providing a pre-operative, virtual depiction of fragmented objects.

As defined medically, the reduction of fractured surfaces includes the restoration of an injured or dislocated object to its pre-fractured anatomical relation. For example, if an object such as a bone is fractured, the resulting surfaces of the fractured bone are oriented such that the fractured pieces are restored to their pre-fractured position with respect to each other. In a non-virtual environment, this reduction typically includes physically manipulating the fragmented bone surfaces to restore the bone fragments to their pre-fractured position.

In a virtual environment, such as the disclosed virtual surgical system, reduction relates to simulating the manipulation of the fragmented objects to provide a reconstructed object in which the fragments are restored to their pre-fractured position. Thus, the resulting "virtual" reduction may provide an image representing the restored object.

In general, one embodiment of a virtual surgical system receives an image, such as a computer tomography (CT) scan, of an area of the patient in need of surgical reconstruction (e.g., in the event of a bone fracture) prior to an incision being made in a surgery. Fragments that are to be reduced are selected using the virtual surgical system. The system performs surface matching techniques using surface data representing the contour of the end surfaces of the fragments to determine how the corresponding fragments should be oriented to perform the reduction. At least one of the fragments may then be transformed (e.g. via translation and/or rotation) to join the surfaces based on the matched surfaces. An image may then be generated of the reconstructed area. Accordingly, the generation of the image of the reconstructed area may occur before an incision is made. Thus, before actual dissection of the area, and the subsequent surgical reduction of the bones, an image of the reconstructed area may be displayed such that a proper prosthesis may be determined and/or manufactured.

Such a system has a number of potential advantages over current surgical procedures which do not provide the capability to preview an image of the reconstructed object. For example, the virtual surgical system minimizes risks to the patient by potentially reducing the amount of dissection required during surgery. Furthermore, the time required for the surgical procedure is potentially reduced by providing the ability to pre-select and/or manufacture an appropriate prosthesis for securing the fragmented (objects once reduced.

Thus, one embodiment of a virtual surgical system includes enabling technology that may incorporate computer vision, computer visualization, and computer-aided design and manufacturing (CAD/CAM) to reconstruct the craniofacial skeleton and reduce the fractures "in silico" (i.e., within a virtual environment created using the computer). Although embodiments are described in the context of performing surgery on a craniofacial skeleton, the virtual surgical system embodiments are not limited to craniofacial applications. Rather, the virtual surgical system may be used for many types of reconstructive surgery, including orthopedic surgery.

FIG. 1 is a schematic diagram that depicts a computer 100 in which embodiments of a virtual surgical system 102 may be implemented. Computer 100 can be a general purpose or special digital computer, such as a personal computer (PC; IBM-compatible, Apple-compatible, or otherwise), workstation, minicomputer, or mainframe computer. The computer 100 may be in a stand-alone configuration or may be networked with other computers. The computer may form part of a CT scanner, x-ray imaging machine, magnetic resonance imaging (MRI) device, sonogram device, a robotic/telerobotic surgical system, or telerobotic surgical interface. The computer 100 includes a display terminal 104 that can provide a graphical model 106 of a CT image. The CT image may depict a portion of the skeletal structure having suffered a fracture, such as the fractured mandible depicted in the graphical model 106 of FIG. 1. Although the graphical model 106 depicts the mandible along one axis, the graphical model 106 can be displayed in a variety of perspectives.

The virtual surgical system 102 can be implemented in software, firmware, hardware, or a combination thereof. In one embodiment, the virtual surgical system 102 is implemented in software, as an executable program that is executed by the computer 100.

Figure 2:
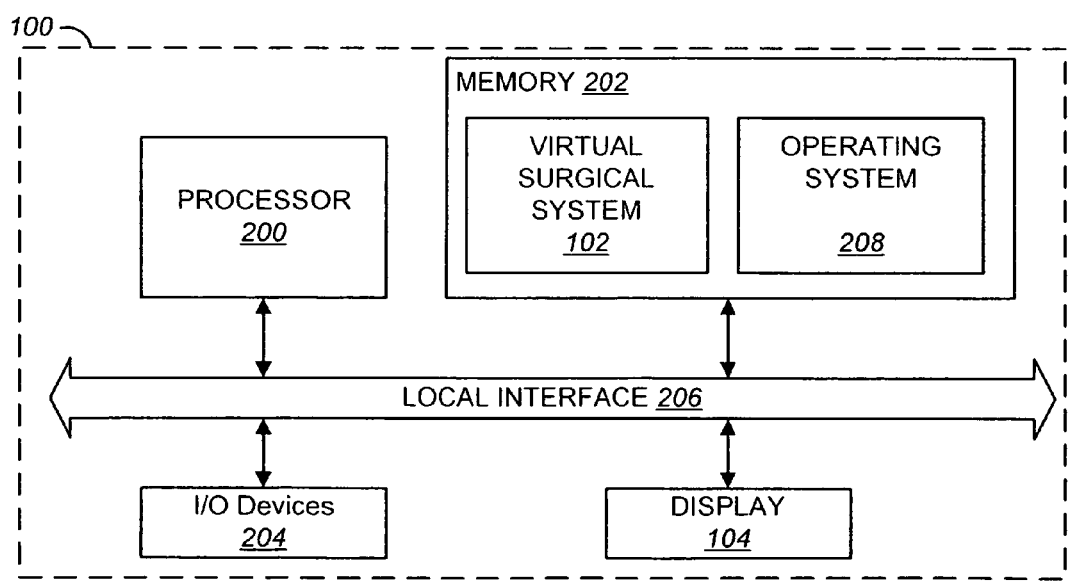
FIG. 2 is a block diagram that illustrates an embodiment of a configuration of the computer shown in FIG. 1 for implementing an embodiment of a virtual surgical system.

FIG. 2 is a block diagram showing an embodiment of a configuration of the computer 100 implementing virtual surgical system 102. Generally, in terms of hardware architecture, computer 100 includes a processor 200, a memory 202, display 104, and one or more input and/or output (I/O) devices 204 (or peripherals) that are communicatively coupled via a local interface 206. The local interface 206 may be, for example, one or more buses or other wired or wireless connections. The local interface 206 may have additional elements such as controllers, buffers (caches), drivers, repeaters, and receivers, to enable communication. Further, the local interface 206 may include address, control, and/or data connections that enable appropriate communication among the aforementioned components. It should be understood that computer 100 may comprise a number of other elements, such as, but not limited to, storage devices, optical drives, and networking hardware, which have been omitted for the purposes of brevity.

Processor 200 is a hardware device for executing software, particularly that which is stored in memory 202. The processor 200 may be any custom made or commercially available processor, a central processing unit (CPU), an auxiliary processor among several processors associated with the computer 100, a semiconductor-based microprocessor (in the form of a microchip or chip set), a macroprocessor, or generally any device for executing software instructions.

Memory 202 may include any one, or a combination of, volatile memory elements (e.g., random access memory (RAM)) and nonvolatile memory elements (e.g., ROM, hard drive, etc.). Moreover, memory 202 may incorporate electronic, magnetic, optical, and/or other types of storage media. Note that the memory 202 may have a distributed architecture in which the various components are situated at locations that are remote from one another but may be accessed by the processor 200.

In addition to memory 202 being used for the storage of data (such as the data corresponding to graphical model 106), memory 202 may include one or more separate executable programs, each of which comprises an ordered listing of executable instructions for implementing logical and arithmetic functions (i.e. software). In the example of FIG. 2, the software in the memory 202 may include an embodiment of the virtual surgical system 102 and a suitable operating system 208. The operating system 208 essentially controls the execution of other computer programs, such as the virtual surgical system 102, and provides scheduling, input-output control, file and data management, memory management, and communication control and related services.

Virtual surgical system 102 may be a source program, executable program (object code), script, or any other entity comprising a set of instructions to be performed. As is described below, the virtual surgical system 102 cart be implemented, in one embodiment, as a distributed network of modules, where one or more of the modules can be accessed by one or more applications or programs or components thereof. In other embodiments, the virtual surgical system 102 can be implemented as a single module with all of the functionality of the aforementioned modules. The source program may be loaded in memory 202 so as to be capable of being executed to operate properly in connection with the operating system 208. Furthermore, virtual surgical system 102 can be written with (a) an object oriented programming language, which has classes of data and methods, or (b) a procedural programming language, which has routines, subroutines, and/or functions, for example but not limited to, C, C++, Pascal, Basic, Fortran, Cobol, Perl, Java, and Ada.

I/O devices 204 may include input devices such as, for example, a keyboard, mouse, scanner, microphone, etc. Furthermore, I/O devices 204 may also include output devices such as, for example, a printer, etc. The I/O devices 204 may further include devices that communicate both inputs and outputs such as, for instance, a modulator/demodulator (modem for accessing another device, system, or network), a radio frequency (RF) or other transceiver, a telephonic interface, a bridge, a router, etc. The I/O devices 204 may also include imaging devices, which may include medical imaging devices, such as, CT imaging devices, X-ray machines, magnetic resonance imaging (MRI) devices, sonogram devices, a robotic/telerobotic surgical system, or telerobotic surgical interface.

When the computer 100 is in operation, processor 200 is configured to execute software stored within the memory 202, to communicate data to and from the memory 202, and to generally control operations of the computer 100 pursuant to the software. The virtual surgical system 102 and the operating system 208, in whole or in part, but typically the latter, are read by the processor 200, perhaps buffered within the processor 200, and then executed.

When the virtual surgical system 102 is implemented in software, as is shown in FIG. 2, it should be noted that the virtual surgical system 102 can be stored on any computer-readable medium for use by, or in connection with, any computer-related system or method. In the context of this document, a computer-readable medium is an electronic, magnetic, optical, or other physical device or means that can contain or store a computer program for use by, or in connection with, a computer related system or method. Virtual surgical system 102 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In an alternative embodiment, where the virtual surgical system 102 is implemented in hardware, virtual surgical system 102 can be implemented with any or a combination of the following technologies, which are each well known in the art: (a) discrete logic circuit(s) having logic gates for implementing logic functions upon data signals, an application-specific integrated circuit (ASIC) having appropriate combinational logic gates, (a) programmable gate array(s) (PGA), a field programmable gate array (FPGA), etc; or can be implemented with other technologies now known or later developed.

Figure 3:
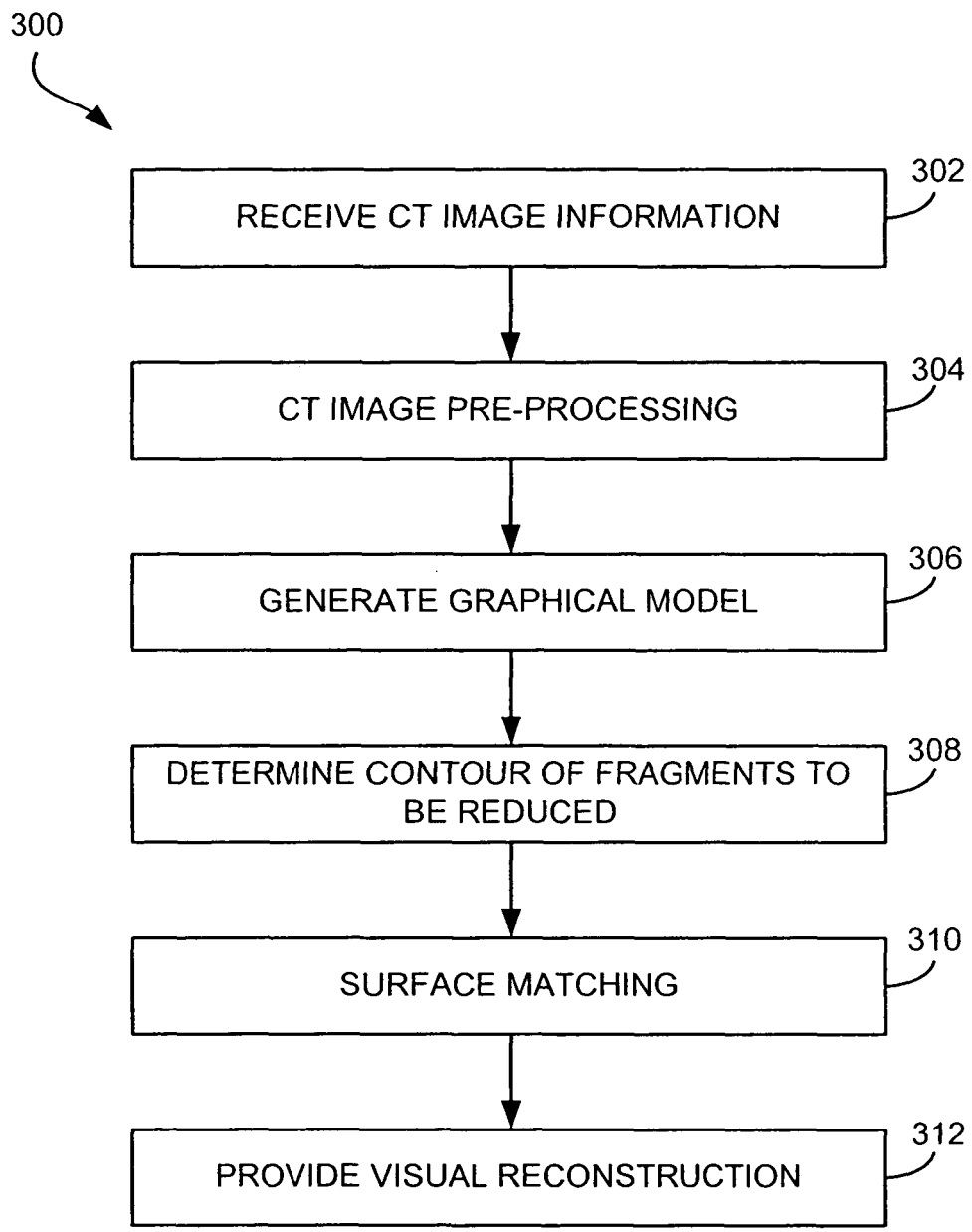
FIG. 3 depicts a flow diagram that illustrates one embodiment of a method employed by the virtual surgical system shown in FIGS. 1 and 2.
Figure 4:
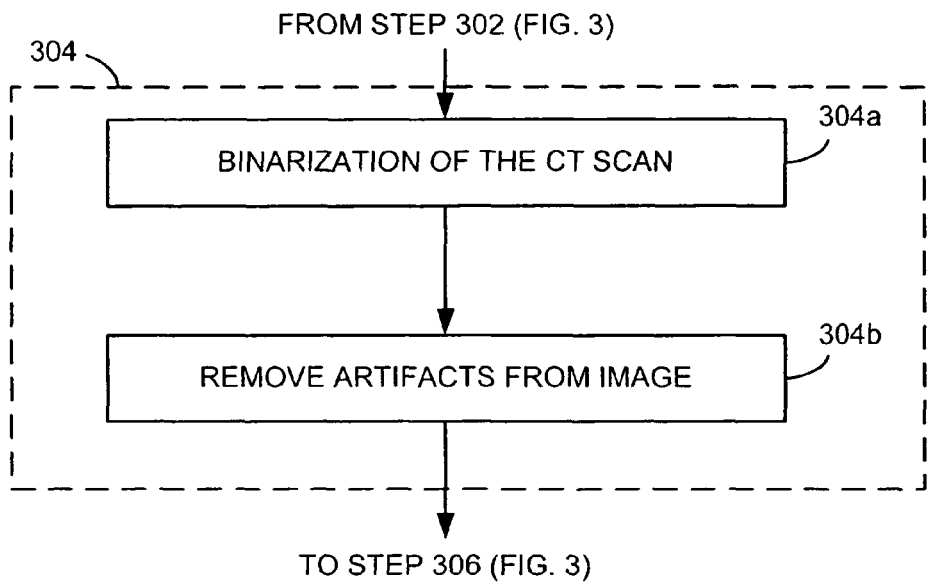
FIG. 4 depicts a flow diagram that illustrates one embodiment of an image pre-processing method that may be used with the method of FIG. 3.

FIG. 3 is a flow diagram that illustrates one embodiment of a method employed by virtual surgical system 102. Any process descriptions, steps, or blocks in flow diagrams should be understood as potentially representing modules, segments, or portions of code which include one or more executable instructions for implementing specific logical functions or steps in the process, and alternate implementations are included within the scope of the preferred embodiments of the virtual surgical system 102 in which functions may be executed out of order from that shown or discussed, including substantially concurrently or in reverse order, depending on the functionality involved, as would be understood by those reasonably skilled in the art.

As depicted in the method embodiment 300, step 302 includes receiving information representing at least one digital image of fragmented bone elements. For example, one input of digital image information to the virtual surgical system 102 may be a sequence of grayscale images of a fractured human mandible. In the present embodiment, the images are two-dimensional (2-D) computer tomography (CT) image slices. In one embodiment, exemplary dimensions and color features for the CT image slices may be 150 millimeter (mm)×150 mm with an 8-bit color depth. The digital image information may be provided, for example, across local interface 206 from input devices 204.

Step 304 includes pre-processing the digital image information (e.g. the CT image). Specifically, as depicted in FIG.

4, in one embodiment, a series of image pre-processing tasks 304a-304b are undertaken by the virtual surgical system 102 before using the surface matching algorithms to obtain the desired goal of reduction (i.e., alignment) of the fracture surfaces. It should be understood that, rather than performing some, or all, of the preprocessing tasks, in some embodiments, pre-processed images may be presented as input to the virtual surgical system 102 at step 302.

One pre-processing task that may be performed by virtual surgical system 102 includes thresholding for binarization of the digital image. That is, a digital image representing objects such as bone fragments may be simplified by determining the objects of interest in the image, and representing those objects with one or more pixel values associated with the object of interest. The objects of interest may be, for example, bone fragments to be joined, but may also include other artifacts, such as objects having densities similar to bone (e.g. other bones, medical instruments, etc.).

Thus, at step 304, according to the present embodiment, the virtual surgical system 102 may classify a pixel with a particular value as belonging to the object of interest. For example, grayscale images assign the number 0 to pure black and the number 255 to pure white. The scale assigns varying shades of gray from dark to light to the whole numbers in between. Thus, in the current embodiment, a grayscale from 0 to 255 levels may represent 256 colors. Accordingly, the virtual surgical system 102 may classify each pixel in a received image with a gray scale value above (or below, in the case of a negative image) a particular level (e.g. 250) to belong to the objects of interest. Any pixel having a value above the threshold level may then be represented using a single color. The threshold value may be selected iteratively by trial and error to arrive at the best representation of the object of interest.

Figure 9:
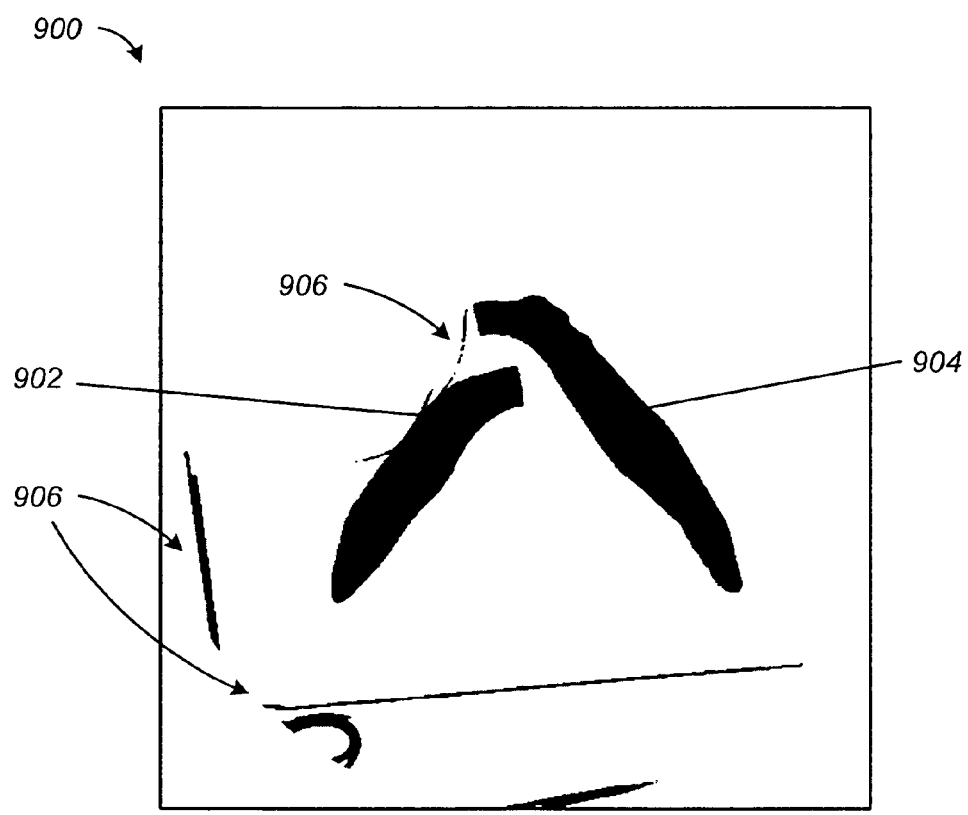
FIG. 9 is a picture of a Computer Tomography (CT) image slice depicting two broken fragments of a human mandible as a result of a thresholding operation performed by the method of FIG. 4.

As an example, a raw CT image slice comprising a number of pixels having grayscale values may undergo the thresholding of step 304, resulting in the binary CT image slice 900 of FIG. 9. Each pixel in the raw CT image slice can be analyzed against a predetermined threshold value of 250. The resulting binary image slice depicts the objects of interest as represented by the single color of black (e.g. a pixel value of 0), and pixels not meeting the threshold are represented by a single color of white (e.g. a pixel value of 1). The resulting binary image B(i, j) for the gray scale CT image slice G(i, j) is given by:

$$B(i, j) = \begin{cases} 0 & \text{if } (G(i, j) > 250 \\ 1 & \text{otherwise} \end{cases} \quad (1)$$

Binarization by itself may not distinctly represent the two fractured fragments 902 and 904, as can be seen from FIG. 9. For example, in some embodiments, undesired artifacts 906, unrelated to the objects of interest, may be represented in the binary CT image 900 (e.g. other bones, medical instruments, etc.). Thus, at step 304b, according to one embodiment, these artifacts may be filtered out of the image. This is beneficial to further simplify the image to represent primarily (or only) the broken fragments that will be later reduced via, for example, surface matching.

Thus, at step 304b, a 2-D connected component labeling (CCL) algorithm, in conjunction with an area filter, may be used to remove (i.e. filter) the unwanted artifacts (which are typically small in size). As is known, a CCL algorithm scans an image and groups the image's pixels into components based on pixel connectivity. That is, the pixels in a connected component may share similar pixel intensity values and are, in some way, connected with each other. Each component may then be separately identified (i.e. labeled). Also, as is known, an area filter may be used to filter out (or include) components having an area value exceeding (or under) a threshold value.

In one implementation, after running the CCL algorithm, connected components with an area less than the threshold value may be deleted from the binary image 900. For example, the threshold value of the area filter can be chosen to be one-thousand pixels, and any individually identified component having a pixel count value less than this is removed from the image. It should be understood that the value of the area filter may be selected based on the size of the image, the size of the bone fragments to be reduced, the type and quantity of artifacts, etc.

Figure 10:
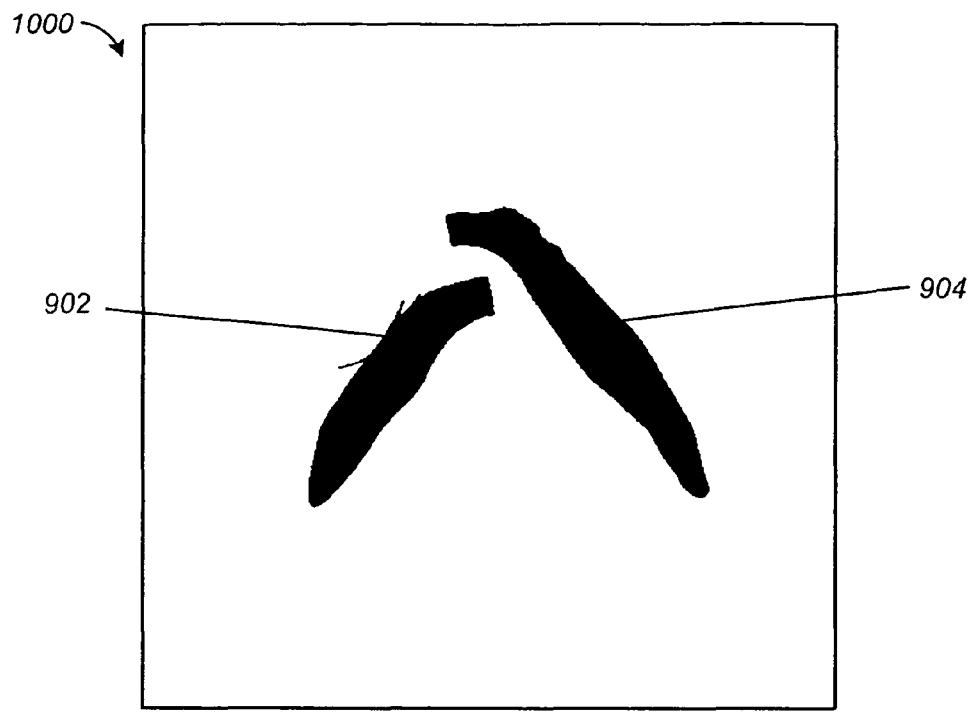
FIG. 10 is a binary image corresponding to the binary image shown in FIG. 9 generated as a result of connected component labeling and size filtering operations performed by the method of FIG. 4.

The result of the processing operations executed in step 304 of FIG. 3 is depicted in the filtered binary image 1000 of FIG. 10. Each of fragments 902 and 904, were identified as components by the CCL algorithm, and thus, were identified as having an area of greater than one-thousand pixels. The artifacts 906 of FIG. 9 were identified as having an area less than one-thousand pixels, and thus, have been removed from the filtered binary image 1000. Each 2-D CT image slice may be processed according to step 304.

At step 306, a three-dimensional (3-D) graphical/volumetric model may be generated from each of the resulting processed two-dimensional CT image slices 900. The model, for example, may be generated by propagating the results of the two-dimensional CCL algorithm along the axial direction, resulting in the identification of the three-dimensional fracture fragments.

At step 308, the virtual surgical system determines the contours of the fragmented/fractured ends of the bone fragments to be reduced in each CT image slice. The contours of the fragmented/fractured ends in the individual CT image slices are collated and represented by a fracture surface data set for each of the fragments. Because the physical surfaces of the corresponding fragmented/fractured ends of bones typically fit together only in a single orientation, these surface data sets may be used to ultimately determine the three-dimensional orientation of the corresponding bone fragments for alignment in the reduction.

In some embodiments, artificial intelligence or other computer algorithms may be incorporated in the virtual surgical system 102 to provide or suggest end-points (and possibly intervening points) corresponding to the contour of the surfaces of the bone fragments. However, in one embodiment, the virtual surgical system 102 uses user-assisted, interactive contour detection to determine the contour of the end points of the fractured bones. That is, user input corresponding to the reconstruction area of the fractured bones is received by the virtual surgical system 102.

Figure 5:
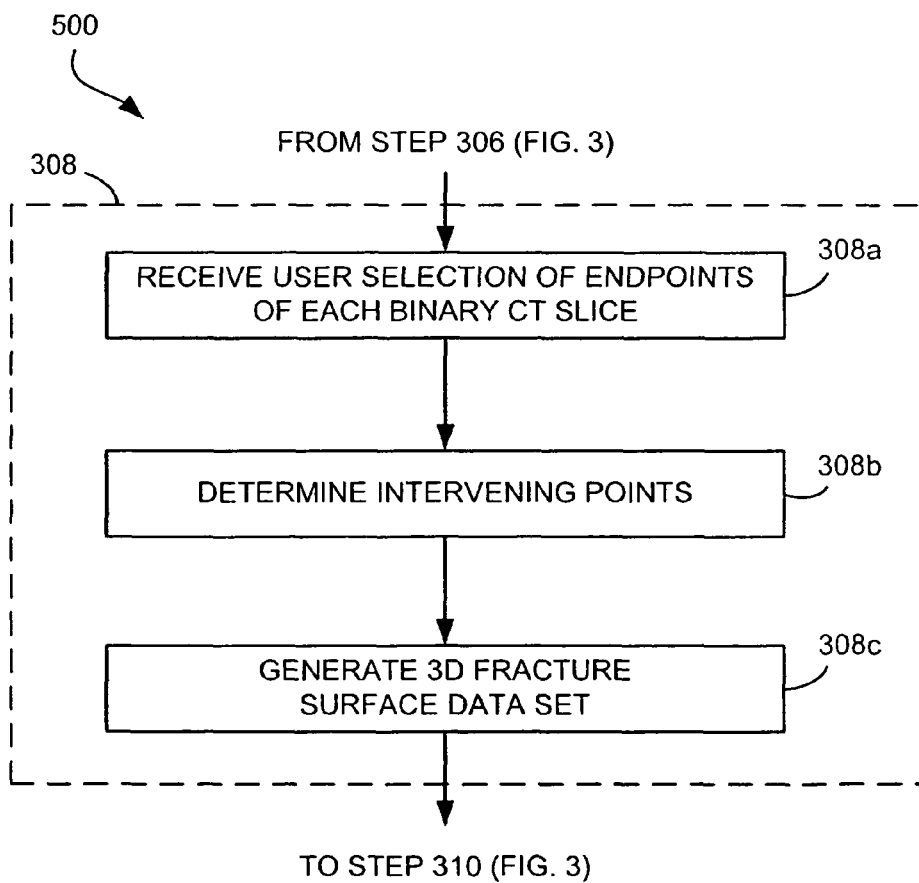
FIG. 5 depicts a flow diagram illustrating one embodiment of a method for selecting fragment contours that may be used with the method of FIG. 3.

FIG. 5 depicts a user-assisted, interactive contour detection embodiment 500, which may be performed to determine the contour as illustrated in step 308 of FIG. 3. At step 308a, a user is iteratively guided through one or more graphical interfaces to select (e.g. via a mouse, stylus, or other input means) end points of a fracture contour in the CT slices. Exemplary user interfaces for the interactive contour detection are described in more detail below with respect to FIGS. 12-14. However, the contour points may be selected, for example, upon the user selection (e.g. a mouse button click, key press, etc.) of a particular area (e.g. a pixel, or group of pixels) according to the position of a cursor (e.g. guided by a mouse or other input device) over the two-dimensional CT scan image. The user performing the selection may, for example, be a surgeon or one skilled in performing such operations. The virtual surgical system 102 collects the data corresponding to the position of these user-selected points.

At step 308b, once the end-points of the fracture contour are selected in each two-dimensional CT slice, the intervening contour points (between the endpoints) may be automatically determined by virtual surgical system 102 at step 308b. For example, the contour points may be generated by system 102 using a contour tracing algorithm. For example, the contour tracing algorithm may be, but is not limited to, a square tracing algorithm, a Moore-neighbor tracing algorithm, radial sweep algorithm, a Theo Pavlidis algorithm, or an active contour fitting using snakes and a Hough Transform.

At step 308c, the contour points, which may include both user-selected end-points and automatically generated intervening points, from the CT image stack (collectively, "three-dimensional fracture surface data") are assembled to generate a three-dimensional fracture surface data set representing the contour of the end surface of the fractured object to be reduced. A three-dimensional fracture surface data set may be generated for each fracture surface (e.g. for each fragment).

Now that each fracture surface is represented by a surface data set, the fragment surfaces can be matched to its corresponding fragment surface. Thus, the surface matching process matches portions of one fragment surface with a corresponding portions of another fragment surface. Once these matching areas (e.g. points) are known, a transformation can be determined that will place one fragment surface in registration with the matched surface of the other fragment. The resulting transformation of the surface can be used to position (e.g. by translation and/or rotation) the entire fragment in its pre-fracture alignment with a corresponding fragment.

Accordingly, looking back to FIG. 3, a surface matching process may be implemented by virtual surgical system 102 at step 310. The surface matching process matches the contours of the end surfaces of each bone fragment to determine orientation of each piece such that the broken ends match and fit together for reduction. In one embodiment, the surface matching process can implemented in the virtual surgical system 102 with either, or both of, an iterative closest point (ICP) algorithm and a Data Aligned Rigidity Constrained Exhaustive Search (DARCES) algorithm. For the purposes of illustration of the implemented ICP and DARCES algorithms, the fragment/data set to be matched is denoted as the sample fragment data set and the fragment data set to which the sample fragment data set is to be matched is denoted as the model fragment data set. Each of the ICP and DARCES algorithms may establish a correspondence between the two surface data point sets to be matched, and may also compute a three-dimensional transformation of one or more of the objects to bring the two surface data point sets into registration.

Figure 6:
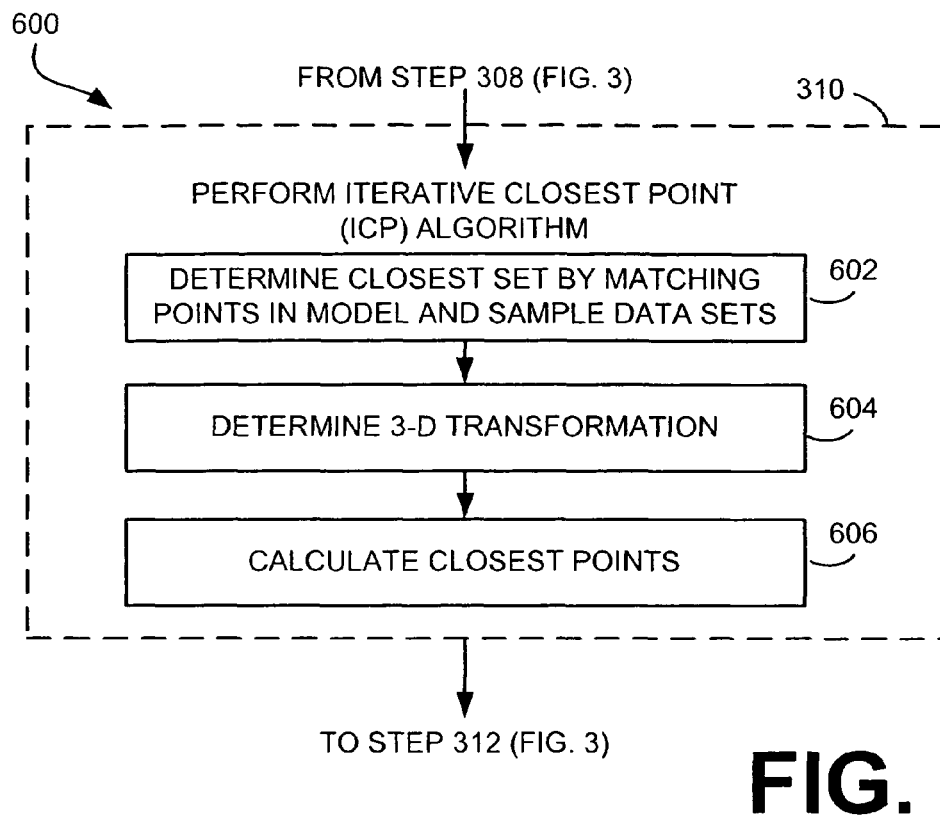
FIG. 6 depicts a flow diagram illustrating one embodiment of an iterative closest point (ICP) algorithm used for surface matching that may be used with the method of FIG. 3.

Looking to FIG. 6, a surface matching algorithm, using ICP process 600 is performed on the sample and fragment data sets. For example, at step 602, the matching points in the model data set corresponding to points in the sample data set are determined. This new set of matching points in the model data set, which represents a subset of the original model data set, is designated as the closest set. Next, at step 604, the three-dimensional rigid body transformation, which may include three-dimensional translation and three-dimensional rotation, that brings the two surfaces into registration (i.e. alignment) is computed. The transformation may, for example, be obtained using the Theory of Quatemions (see, e.g., P. J. Besl and N. D. McKay, "A Method for Registration of 3-D Shapes", *IEEE Trans. Pattern Analysis and Machine Intelligence,* 14(2), 1992, pp. 239-255, herein incorporated by reference). Once calculated, the computed transformation is applied to the original sample fragment data set.

At step 606, the mean squared error (MSE) between the transformed sample data points (from step 604) and the corresponding closest points in the closest set is calculated. The MSE ($\epsilon^2$) is given by:

$$\varepsilon^2 = 1/N \sum_{i=1}^{N} \|c_i - Rs_i + T\|^2 \quad \text{(Eq. 2)}$$

where R denotes the rotation, T denotes the translation, $s_i$ denotes a point of the sample data set and $c_i$ represents the corresponding point in the closest set.

Figure 11:
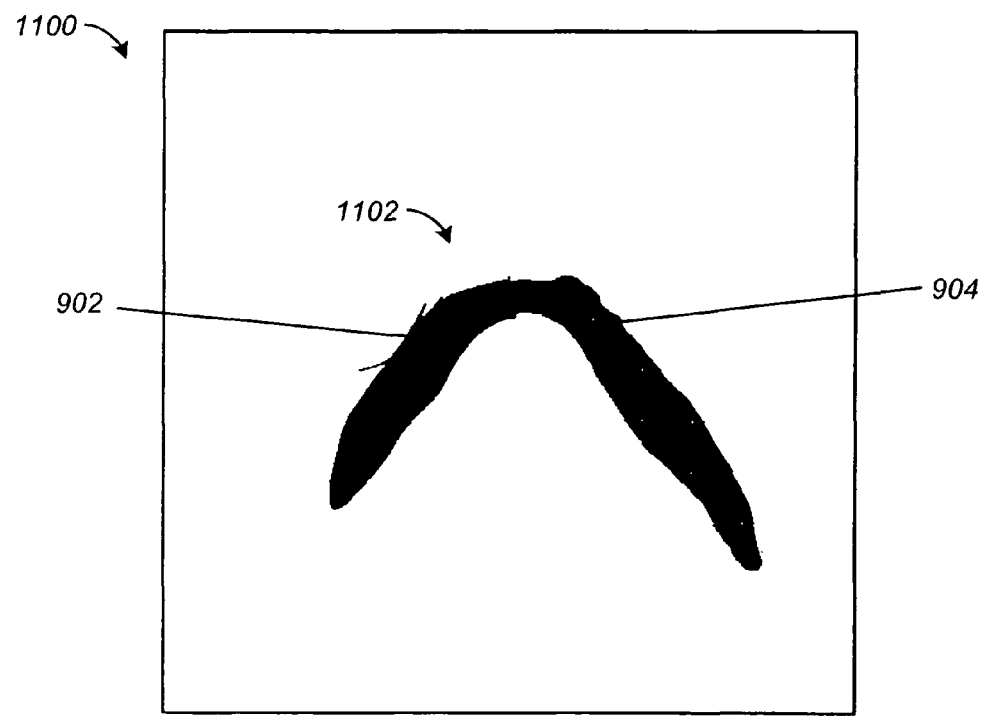
FIG. 11 is a binary image corresponding to the binary image shown in FIG. 10 generated as a result of a two-dimensional contour matching operation.

Steps 602-604 are repeated with an updated sample set (generated by applying R and T obtained at the current iteration to the current sample set) until a pre-specified error convergence criterion is reached. As depicted in FIG. 11, a CT image scan slice 1100 depicts bone fragment 902 after being transformed according to the transformation obtained satisfying the pre-specified convergence criterion. Thus, the resulting reduced bone 1102 comprises bone fragment 902, having been transformed to be aligned with bone fragment 904.

To compute the closest set at step 602, the matching point pairs can be determined using the Maximum Cardinality Minimum Weight Bipartite Matching (MCMW) algorithm based on the Hungarian method proposed by Kuhn (see H. W. Kuhn, "The Hungarian method for the assignment problem," *Nav. Res. Log. Quart.* 2, 1955, herein incorporated by reference).

For a Bipartite Graph G(V, E) with vertex set V and edge set E, the 3-D sample and model data sets correspond to the two disjoint vertex subsets (V1, V2) of the vertex set V. The edge-weight ($W_{ij} \epsilon E$) between any two nodes i and j (such that i$\epsilon$V1 and j$\epsilon$V2) is deemed to be the Euclidean distance between them. Note that the Euclidean distance is invariant to a 3-D rigid body transformation. Thus, the edge weights are given by $$W_{ij} = [(x_i - x_j)^2 + (y_i + y_j)^2 + (z_i - z_j)^2]^{1/2} \quad \text{(Eq. 3)}$$

In some embodiments, further enhancements to the MCMW algorithm may be made. For example, the objective function of Eq. 3 may be modified using a reward-penalty scheme to take into account the surface irregularities on the two fracture surfaces. Using a reward/penalty scheme, edge weights ($W_{ij}$) between the two corresponding points i and j in Eq. 3 may be updated by adding a penalty term ($\text{Penalty}_{ij}$) to the Euclidean Norm ($\text{Enorm}_{ij}$):

$$W_{ij} = \text{Enorm}_{ij} + \lambda \text{Penalty}_{ij} \quad \text{(Eq. 4)}$$

where $\lambda$ is the penalty coefficient.

In a first approach, the signs of the mean and Gaussian surface curvature are used to classify points on the fracture surfaces into primitive surface categories. Corresponding surface points on the opposable fracture surfaces are rewarded if they belong to compatible surface types, and penalized otherwise.

In a second approach, the surface points are assigned membership values to the two fuzzy sets "bulge" and "droop." Corresponding surface points on the opposable fracture surfaces are rewarded based on their membership values within the same fuzzy set, and penalized otherwise.

Each of these approaches are detailed more specifically in Bhandarkar, S. M., Chowdhury A. S., Tollner, E. W., Yu, J. C., Ritter, E. W., and Konar, A. 2005a. Surface Reconstruction for Computer Vision-based Reconstructive Surgery. *Proc. IEEE Workshop on Applications of Computer Vision* (WACV 2005), Breckenridge, Colo., Jan. 5-7, pp. 257-262, which is incorporated by reference.

Further, the minimum mean squared surface matching error criterion for optimal reconstruction may be enhanced to include additional shape-based and/or biomechanical stability-based criteria. For craniofacial surgery, this additional shape-based and/or biomechanical stability-based criteria may be the 3-D shape symmetry of the reconstructed mandible, maximum smoothness and continuity of the reconstructed mandibular surface and minimum surface strain energy, and the minimum surface area for the reconstructed mandibular surface.

Now that various ICP algorithm embodiments have been discussed, attention is now directed to embodiments of a DARCES algorithm which may be used to perform the surface matching step 310 of FIG. 3. Looking to FIG. 7, DARCES algorithm 700, may be used alone, or in combination with, ICP algorithm 600. DARCES algorithm 700 may be used for solving a partially overlapping three-dimensional surface registration problem efficiently and reliably. It is assumed that one skilled in the art understands the general concepts of implementing DARCES algorithms (see, for example, C. S. Chen, "RANSAC-Based DARCES: A New Approach to Fast Automatic Registration of Partially Overlapping Range Images", *IEEE Trans. Pattern Analysis and Machine Intelligence*, 21(11), 1999, pp. 1229-1234, herein incorporated by reference).

The DARCES method does not require local feature detection and does not require initial transformation estimation for the matching of the two 3-D data sets. Thus, DARCES algorithms differ from any feature-based approach or iterative approach for performing the 3-D surface matching (i.e., 3-D surface registration).

Figure 7:
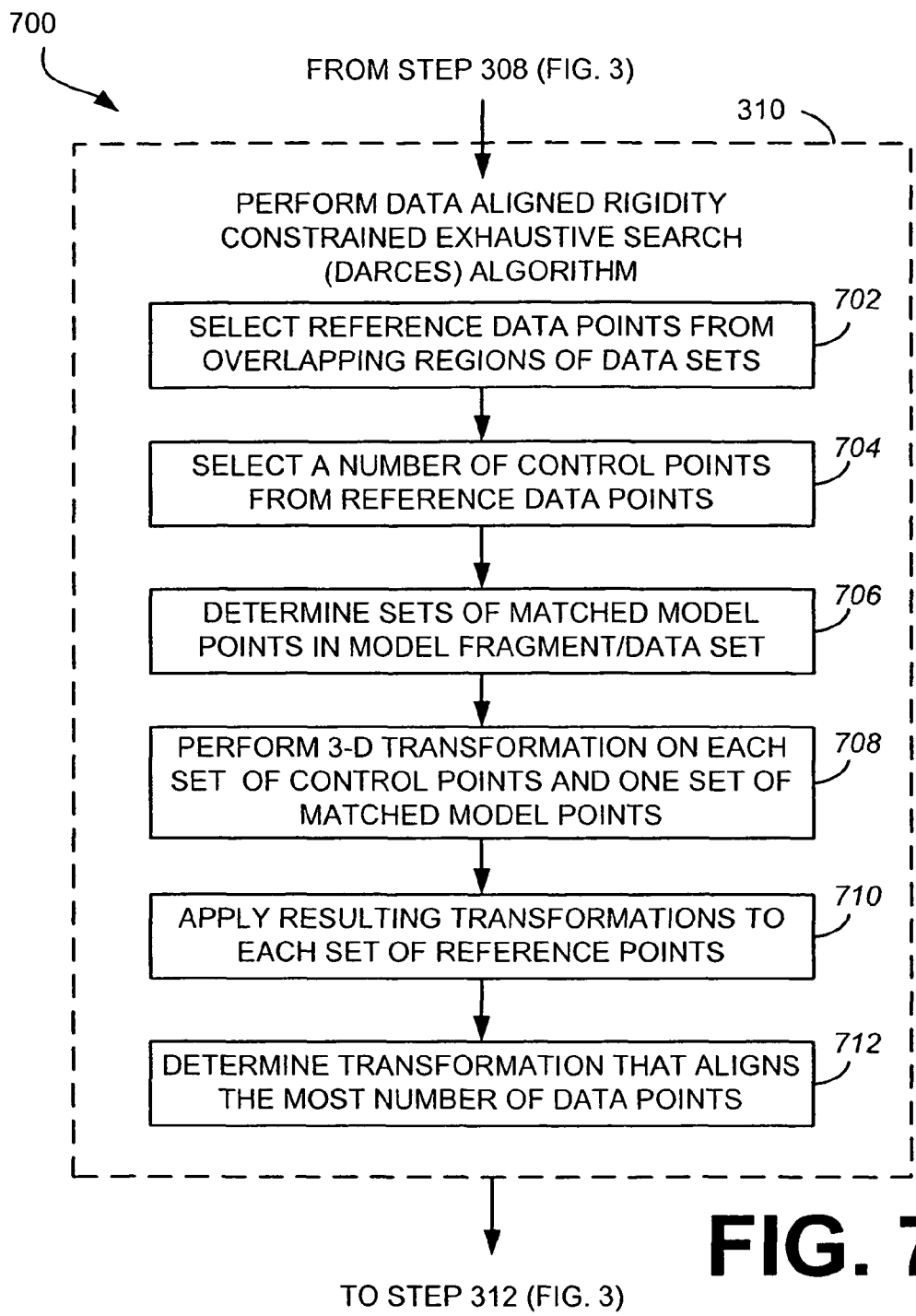
FIG. 7 depicts a flow diagram illustrating one embodiment of a Data Aligned Rigidity Constrained Exhaustive Search (DARCES) algorithm used for surface matching that may be used with the method of FIG. 3.

Looking to FIG. 7, at step 702, reference points are exhaustively selected from the sample data set representing the common set of CT image slices in the CT image stack. The CT images include both the opposable fracture surfaces, represented by the sample data set and the model data set, respectively.

At step 704, a number of control points are chosen from the set of selected reference points. Control points may be described as those that, if matched with corresponding points in the model data set, would enable a three-dimensional rigid body transformation (which may include three-dimensional rotation and three-dimensional translation) to be computed. Control points may be chosen, for example, using an improvised Random Sample Consensus (RANSAC) based approach.

In the present embodiment, for example, three control points are selected. Although three points are selected, in other embodiments, more may be selected. The three control points may be selected according to geometrical constraints. For example, the control points may be selected such that they form an equilateral triangle. According to one embodiment, the length of a side of the triangle may be varied between 25%-35% of the maximum spread of the reference data set. The alignment thresholds are chosen to be different along each coordinate axis. Along each of the x, y, z axes, the alignment thresholds may be chosen to be equal to the respective voxel resolutions.

Once a set of control points are selected from the reference points of the sample fragment data set, at step 706 a set of corresponding three matching points on the model data set (herein, "matched model points") are determined such that they satisfy the same inter-point constraints as the set of three control points. Typically, for the three reference points, there will be a number of such sets of three matched model points in the model fragment data set. Each of these matchings may be enumerated and the best match selected as described below.

At step 708, for each set of three pairs of corresponding points (i.e. each set of three control points and one set of three matched model points), a three-dimensional rigid body transformation is obtained, which may include a translational and rotational component. For determining the rotational component of the three-dimensional rigid body transformation, the Singular Value Decomposition (SVD) technique may be employed (see K. S. Arun, T. S. Huang and S. D. Blostein "Least-Squares Fitting of Two 3-D Point Sets", *IEEE Trans. Pattern Analysis and Machine Intelligence*, 9(5), 1987, pp. 698-700, herein incorporated by reference). Note that three pairs of corresponding points are sufficient to determine a three-dimensional rigid body transformation.

At step 710, each transformation is then applied to all the reference points in the sample fragment data set, other than the three control points. If the distance between a transformed reference point and its nearest matched model point is below a predetermined threshold, then this reference point is considered to have been successfully aligned or matched with the model surface. Thus, the number of successfully aligned sample data points in the sample fragment data set is computed for each transformation. At step 712, the transformation that successfully aligns the most number of sample data points with the model surface data set is deemed to be the solution (e.g. the closest transformation) to the surface matching problem.

Now that ICP and DARCES algorithm approaches have been described that can be used with the virtual surgical system, it is helpful to understand the inherent advantages of each approach. For example, the DARCES algorithm is useful with outlier (e.g., noise or noisy data) rejection, but the resulting three-dimensional rigid body transformation computed by the DARCES algorithm is, in general, not as precise as the ICP algorithm. The ICP algorithm, on the other hand, generally yields a more accurate three-dimensional rigid body transformation but can be sensitive to outliers in the input data. Thus, using the ICP algorithm, the presence of outliers may cause inaccurate computer estimates during the transformation computation process. Moreover, the pairs of matched points generated by the DARCES algorithm also helps in reducing the cardinalities of the two data sets to be matched (using Bipartite Graph Matching) in the ICP algorithm (see N. Christofides, *Graph Theory An Algorithmic Approach*. Academic Press, 1975. pp. 372-379, herein incorporated by reference). Thus, the dense bipartite graph used to determine the closest set in the ICP algorithm can be reduced to a sparse bipartite graph with fewer nodes and edges (see W. Kim and A. C. Kak, "3-D Object Recognition Using Bipartite Matching Embedded in Discrete Relaxation", *IEEE Trans. Pattern Analysis and Machine Intelligence*, 13(3), 1991, pp. 224-251, herein incorporated by reference). The subsequent MCMW algorithm has a much reduced computational complexity when run on a sparse bipartite graph. Simultaneously, a much lower MSE can be achieved for the matching of the two surfaces, since the DARCES algorithm provides a better starting point to the ICP algorithm by virtue of outlier removal. Thus, the synergetic combination of the DARCES and ICP algorithms, where the inputs to the ICP algorithm are the original model set and the sample set transformed by the DARCES algorithm, results in an improved surface matching algorithm with a substantial reduction in the mean squared error (MSE) (e.g. higher reconstruction accuracy) and reduced execution time for the reconstruction of the craniofacial skeleton.

Figure 8:
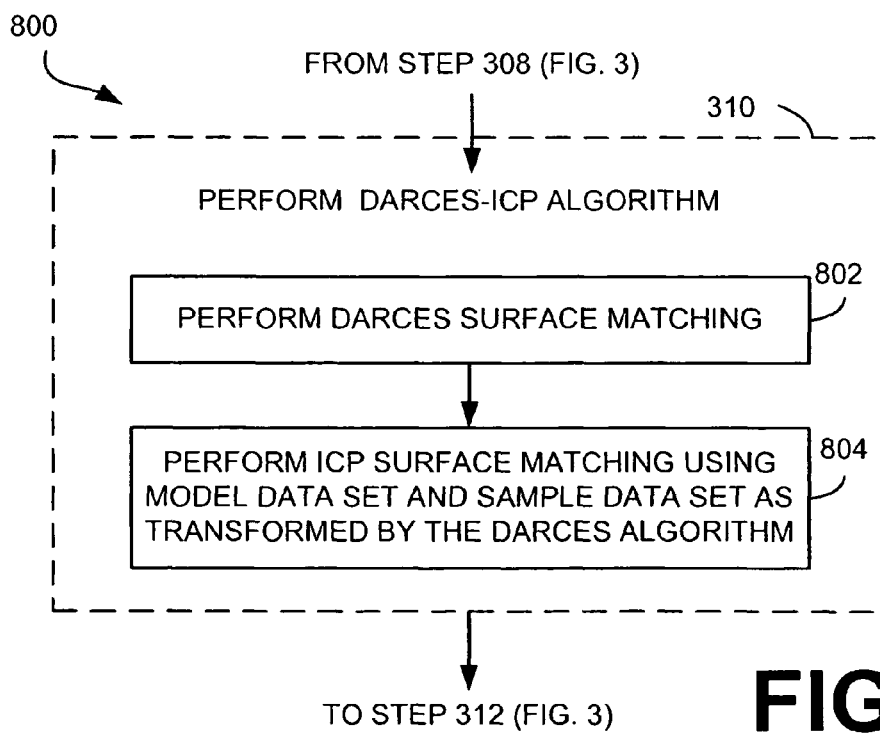
FIG. 8 depicts a flow diagram illustrating one embodiment of a combined ICP-DARCES algorithm used for surface matching that may be used with the method of FIG. 3.

Accordingly, as depicted in FIG. 8, one embodiment of virtual surgical system 102 performs the surface matching step 308 of FIG. 3 using a DARCES-ICP algorithm 800 that, as implied by the name, synergistically includes a combination of the DARCES algorithm and an ICP algorithm. At step 802, the DARCES algorithm is performed (e.g. see FIG. 7) using the sample and model data sets of the original fragmented surfaces. The DARCES algorithm produces a transformed sample fragment data set representing the transformation required to bring the surfaces to their pre-fractured positions.

At step 804, an ICP algorithm (e.g. see FIG. 6) may be performed using the transformed sample data fragment set generated by the DARCES algorithm of step 802. Thus, it may be said that, according to this embodiment, the output of the DARCES algorithm is fed as input to the ICP algorithm.

Evaluations between the surface matching results from the ICP, DARCES and DARCES-ICP algorithms have been performed. Comparison of the MSE metric for the matched surfaces for each of the above algorithms shows that the DARCES-ICP hybrid algorithm yields a lower MSE metric than both the ICP and DARCES algorithms. The DARCES and ICP algorithms are purely data driven. In practice, in addition to obtaining a locally optimal solution, the preservation of the global three-dimensional shape of the human mandible is very much desirable.

Thus, looking back to FIG. 3, at step 312, a visual reconstruction is provided. For the visual reconstruction step, a three-dimensional image of the reconstructed area may be generated. The generated three-dimensional image may, for example, be displayed on display 104, or transmitted to another suitable display, for providing a depiction of the fragmented parts, as reduced to their pre-fracture orientation, according to the surface matching performed at step 310. This three-dimensional visual representation enables a surgeon, or other skilled practitioner, to determine the type and configuration of a prosthesis to use to secure the reduced fragments in place without having to see the actual bone fragments (e.g. after dissection in surgery).

In some embodiments, the virtual surgical system 102 may incorporate expert system technology (e.g., artificial intelligence) to provide a three-dimensional image of the reconstructed area together with a recommended prosthesis or prostheses for joining, for example, the fractured bone fragments. In other words, some embodiments of the virtual surgical system 102 may suggest, for example, any of one or more types of prostheses, the configuration of the prosthesis (e.g. what the prostheses should look like), a proposed location of the prostheses with respect to the reduced bone fragments, and how the prostheses should be used.

Now that the general functionality of the virtual surgical system has been described, attention is now directed to a number of graphical user interfaces which may be used to implement portions of the virtual surgical system. The graphical user interfaces may, for example, be displayed on display 104 (FIGS. 1-2) and provide an interface between a user and the virtual surgical system 102.

Figure 12:
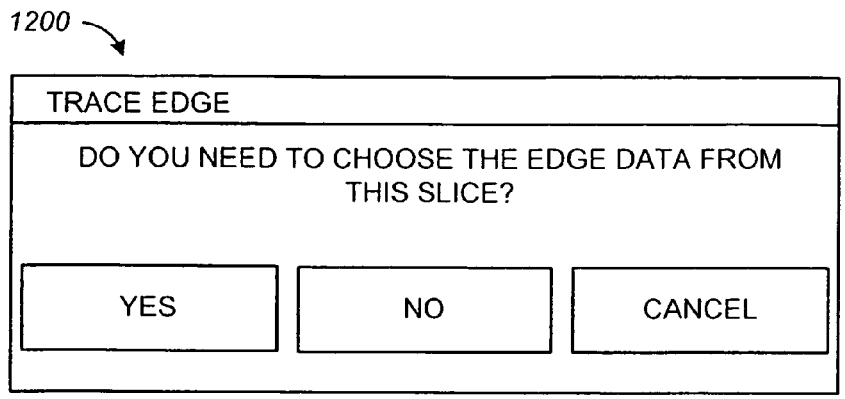
FIGS. 12-14 depict embodiments of graphical user interfaces for enabling a user to cooperate with the virtual surgical system of FIG. 1 to extract surface contour data from each CT image scan slice.

Looking to FIG. 12, a graphical user interface 1200 depicts a first interface displayed during the interactive contour detection process of step 308a of FIG. 5. Graphical user interface 1200 requests a user's decision as to whether edge data (e.g. contour endpoints of a fragmented object) should be collected from a particular image slice. After user interface 1200 is displayed, the user may respond by selecting a YES button icon, a NO button icon, or a CANCEL button icon. If the user response is No, the interface program fetches the next binary CT image slice and asks the same question. If the answer is Cancel, the current functionality is forcibly aborted, If the user responds Yes, the interface of FIG. 13 may be displayed.

Figure 13:
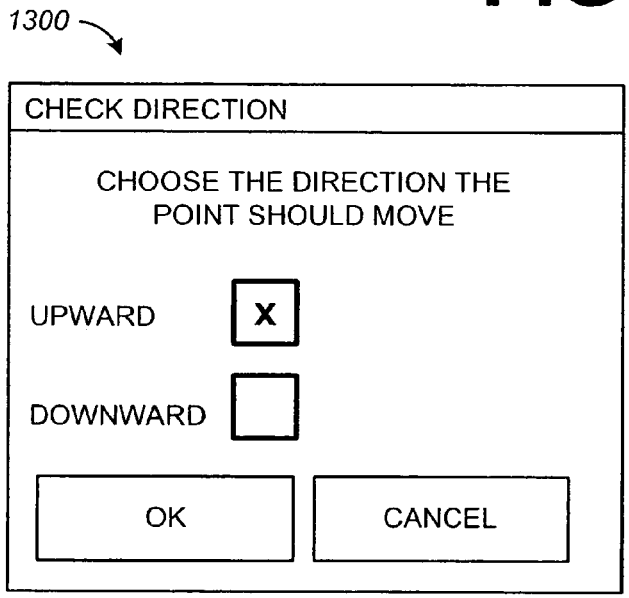

FIG. 13 depicts a menu 1300 used to select end-points of a contour fracture of one of the broken fragments via, for example, a mouse click. The menu screen in FIG. 13 provides the user the needed flexibility in the event that the mouse clicks are not accurate enough. Thus, after selecting a point on the image with the mouse, the user can specify a direction (by checking the UPWARD or DOWNWARD option, for example) in which the clicked point needs to be adjusted in order to provide more precise selection of the edge point on the fracture contour. Although only an upward-downward adjustment is provided in the embodiment of FIG. 13, it should be understood that a left and/or right adjustment may also be provided, and the menu may be modified and customized according to a users requirements. The user presses the OK button to proceed.

Figure 14:
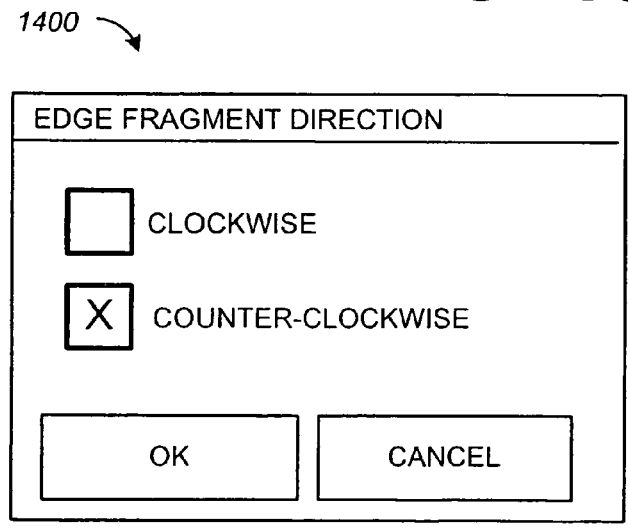

Once the reference points (i.e., the topmost and bottommost points) along the fracture contour are determined using menu 1300 of FIG. 13, the user may specify the contour tracing direction (e.g. step 308b of FIG. 5) namely, CLOCKWISE or COUNTER-CLOCKWISE using the menu depicted in FIG. 14. Once the fracture contour is traced in the specified direction, the user may presses the OK button to permit the data acquisition for the binary CT image slice under consideration. Once the surface data acquisition from one fracture fragment from all the slices is completed, the same process can be repeated for the other broken fragment(s).

It should be emphasized that the above-described embodiments, particularly, any "preferred" embodiments, are merely possible examples of implementations, merely set forth for a clear understanding of the principles of the virtual surgical system. Many variations and modifications may be made to the above-described embodiment(s) without departing substantially from the spirit and principles of the disclosure.

At least the following is claimed:

1. A method for providing virtual alignment of fractured bones comprising:
    capturing image data of fragments of a bone that were separated due to bone fracture;
    pre-processing the image data by:
        comparing a value of each pixel in the image data to a threshold value;
        setting the value of each pixel in the image data that is above the threshold value to a first single pixel value;
        identifying objects in the image data based on pixel connectivity; and
        filtering identified objects having an area less than a predetermined value from the image data;
    generating three-dimensional models of the bone fragments from the image data;
    determining contours of fractured ends of the bone fragments;
    matching the fractured ends of the bone fragments;
    determining a transformation that places the fractured ends in three-dimensional alignment to form a reconstructed bone; and
    generating an image of the reconstructed bone that results from the transformation.

2. The method of claim 1, wherein determining the transformation includes determining at least one component selected from the group consisting of a translational component and a rotational component.

3. The method of claim 1, wherein matching the fractured ends includes applying a surface matching algorithm selected from the group consisting of: an iterative closest point (ICP) surface matching algorithm and a data aligned rigidity constrained exhaustive search (DARCES) surface matching algorithm.

4. The method of claim 1, wherein surface data of each of the fractured ends forms a surface data set for each of the fractured ends, and matching the fractured ends includes:
    matching the fractured ends with a data aligned rigidity constrained exhaustive search (DARCES) surface matching algorithm using the surface data sets to produce a transformed sample data set for at least one of the fractured ends; and
    matching the fractured ends with a closest point (ICP) surface matching algorithm using the transformed sample data set.

5. The method of claim 1, further comprising displaying the image of the reconstructed bone.

6. The method of claim 1, wherein the computing device is selected from a group consisting of: a computer tomography (CT) scanner, an x-ray machine, a medical imaging device, a magnetic resonance imaging (MRI) device, a sonogram device, a robotic surgical system, a telerobotic surgical system, and a telerobotic surgical interface.

7. The method of claim 1, further comprising generating a contour surface data set corresponding to each of the fractured surfaces.

8. The method of claim 7, wherein generating the contour surface data set comprises:
    receiving a plurality of user selected endpoints; and
    determining a plurality of intervening points between the user selected endpoints.

9. A virtual surgical system comprising:
    a memory including instructions for providing virtual alignment of bone fragments; and
    a processor configured to execute the instructions to:
    receive captured image data of the bone fragments;
    pre-process the image data by:
        comparing the value of each pixel in the image data to a threshold value;
        setting the value of each pixel in the image data that is above the threshold value to a first single pixel value;
        identifying objects in the image data based on pixel connectivity; and
        filtering identified objects having an area less than a predetermined value from the image data;
    generate three-dimensional models of the bone fragments;
    determine contours of fractured ends of the bone fragments;
    match the fractured ends of the bone fragments;
    determine a transformation that places the fractured ends in three-dimensional alignment to form a reconstructed bone; and
    generate an image of the reconstructed bone that results from the transformation.

10. The virtual surgical system of claim 9, wherein the processor is further configured to:
    determine the transformation by determining at least one component selected from the group consisting of: a translational component and a rotational component.

11. A virtual surgical system of claim 9, wherein the processor is further configured to match the fractured ends with a surface matching algorithm selected from the group consisting of: an iterative closest point (ICP) surface matching algorithm and a data aligned rigidity constrained exhaustive search (DARCES) surface matching algorithm.

12. The virtual surgical system of claim 9, wherein surface data of each of the fractured ends forms a surface data set for each fractured ends, and wherein the processor is further configured to:
    match the fractured ends by matching the fractured ends with a data aligned rigidity constrained exhaustive search (DARCES) surface matching algorithm using the surface data sets to produce a transformed sample data set for at least one of the fractured ends; and match the fractured ends with a closest point (ICP) surface matching algorithm using the transformed sample data set.

13. The virtual surgical system of claim 9, further comprising an output device for displaying the image of the reconstructed bone.

14. The virtual surgical system of claim 9, wherein the virtual surgical system forms at least part of a device selected from the group consisting of: a computer, a computer tomography (CT) scanner, an x-ray machine, a medical imaging device, a magnetic resonance imaging (MRI) device, a sonogram device, a robotic surgical system, a telerobotic surgical system, and a telerobotic surgical interface.

15. The virtual surgical system of claim 9, wherein the processor is further configured to generate a contour surface data set corresponding to each of the fractured ends.

16. The virtual surgical system of claim 15, wherein the processor is further configured to generate the contour surface data set by:
    receiving a plurality of user selected endpoints; and
    determining a plurality of intervening points between the user selected endpoints.

17. A non-transitory computer-readable memory that stores a computer program for providing virtual alignment of bone fragments comprising:
    logic configured to generate three-dimensional models of bone fragments that were separated due to bone fracture;
    logic configured to compare the value of each pixel in the image data to a threshold value;
    logic configured to set the value of each pixel in the image data that is above the threshold value to a first single pixel value;
    logic configured to identify objects in the image data based on pixel connectivity;
    logic configured to filter identified objects having an area less than a predetermined value from the image data;
    logic configured to determine contours of fractured ends of the bone fragments;
    logic configured to match the fractured ends of the bone fragments;
    logic configured to determine a transformation that places the fractured ends in three-dimensional alignment to form a reconstructed bone; and
    logic configured to generate an image of the reconstructed bone that results from the transformation.

18. The non-transitory computer-readable memory of claim 17, wherein the logic configured to determine the transformation includes logic configured to determine at least one component selected from the group consisting of: a translational component and a rotational component.

19. The non-transitory computer-readable memory of claim 17, wherein the logic configured to match the fractured ends includes a surface matching algorithm selected from the group consisting of: an iterative closest point (ICP) surface matching algorithm and a data aligned rigidity constrained exhaustive search (DARCES) surface matching algorithm.

20. The non-transitory computer-readable memory of claim 17, wherein the surface data of each of the fractured ends forms a surface data set for each fragment surface, and the logic configured to match the fractured ends includes:

logic configured to match the fractured ends with a data aligned rigidity constrained exhaustive search (DARCES) surface matching algorithm using the surface data sets to produce a transformed sample data set for at least one of the fractured ends; and logic configured to match the fractured ends with a closest point (ICP) surface matching algorithm using the transformed sample data set.

21. The non-transitory computer-readable memory of claim 17, further comprising logic configured to display the image of the reconstructed bone.

22. The non-transitory computer-readable memory of claim 17, further comprising logic configured to generate a contour surface data set corresponding to each of the fractured surfaces.

23. The non-transitory computer-readable memory of claim 22, wherein the logic configured to generate the contour surface data set comprises:

logic configured to receive a plurality of user selected endpoints; and logic configured to determine a plurality of intervening points between the user selected endpoints.

* * * * *